(12) United States Patent
Matsumoto et al.

(10) Patent No.: US 11,141,486 B2
(45) Date of Patent: Oct. 12, 2021

(54) DRUG DELIVERY DEVICE

(71) Applicant: National University Corporation Tokyo Medical and Dental University, Tokyo (JP)

(72) Inventors: Akira Matsumoto, Tokyo (JP); Hiroko Matsumoto, Tokyo (JP); Takayoshi Suganami, Tokyo (JP); Miyako Tanaka, Tokyo (JP); Yuji Miyahara, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 15/770,125

(22) PCT Filed: Oct. 24, 2016

(86) PCT No.: PCT/JP2016/081407
§ 371 (c)(1),
(2) Date: Apr. 20, 2018

(87) PCT Pub. No.: WO2017/069282
PCT Pub. Date: Apr. 27, 2017

(65) Prior Publication Data
US 2018/0333495 A1  Nov. 22, 2018

(30) Foreign Application Priority Data

Oct. 23, 2015  (JP) .............................. JP2015-209192

(51) Int. Cl.
*A61K 47/32* (2006.01)
*A61K 38/28* (2006.01)
(Continued)

(52) U.S. Cl.
CPC ............ *A61K 47/32* (2013.01); *A61K 9/0004* (2013.01); *A61K 9/70* (2013.01); *A61K 38/28* (2013.01);
(Continued)

(58) Field of Classification Search
CPC ...... A61K 47/32; A61K 9/0004; A61K 38/28; A61K 9/70; A61K 47/16; C08F 220/56;
(Continued)

(56) References Cited

U.S. PATENT DOCUMENTS 5,683,584 A * 11/1997 Wenthold ............... B01D 61/30
210/500.23
6,960,617 B2 * 11/2005 Omidian .............. A61K 9/0065
521/102
(Continued)

FOREIGN PATENT DOCUMENTS

JP  04-282310 A  10/1992
JP  H11-513041 A  11/1999
(Continued)

OTHER PUBLICATIONS

International Search Report dated Nov. 15, 2016, in PCT/JP2016/081407.

*Primary Examiner* — Robert A Wax
*Assistant Examiner* — Quanglong N Truong
(74) *Attorney, Agent, or Firm* — Foley & Lardner LLP

(57) ABSTRACT

An improved device capable of releasing a drug in response to stimuli such as a glucose concentration is provided. Provided is a drug delivery device, including a porous body such as a hollow fiber having biocompatibility and drug permeability, a stimuli-responsive gel composition filling inside of the porous body, and a drug surrounded by the gel composition inside of the porous body.

15 Claims, 12 Drawing Sheets

A

B

(51) Int. Cl.
  *A61M 5/32* (2006.01)
  *A61M 5/142* (2006.01)
  *A61K 9/00* (2006.01)
  *A61K 9/70* (2006.01)
  *A61M 25/00* (2006.01)
  *A61M 37/00* (2006.01)
  *C08F 220/56* (2006.01)
  *A61K 47/16* (2006.01)

(52) U.S. Cl.
  CPC ........ *A61M 5/14248* (2013.01); *A61M 5/329* (2013.01); *A61M 25/0043* (2013.01); *A61M 37/0015* (2013.01); *C08F 220/56* (2013.01); *A61K 47/16* (2013.01); *A61M 5/3291* (2013.01); *A61M 2025/0057* (2013.01); *A61M 2205/0238* (2013.01); *C08F 2800/10* (2013.01)

(58) Field of Classification Search
  CPC .. C08F 2800/10; A61M 5/24; A61M 37/0015; A61M 25/0043; A61M 5/3291; A61M 5/329; A61M 5/14248; A61M 2025/0057; A61M 2205/0238; A61P 3/10
  See application file for complete search history.

(56) References Cited

U.S. PATENT DOCUMENTS

| | | | |
|---|---|---|---|
| 2004/0028655 A1* | 2/2004 | Nelson | A61L 31/145 424/93.2 |
| 2004/0265386 A1* | 12/2004 | Taylor | A61K 9/0014 424/486 |
| 2011/0212495 A1* | 9/2011 | Diner | C12M 29/18 435/99 |
| 2012/0046651 A1* | 2/2012 | Beyer | A61B 5/14503 604/891.1 |
| 2012/0283403 A1 | 11/2012 | Matsumoto et al. | |
| 2013/0066264 A1 | 3/2013 | Matsumoto et al. | |
| 2015/0150796 A1* | 6/2015 | Duggan, Jr. | C12N 5/0621 424/427 |

FOREIGN PATENT DOCUMENTS

| | | |
|---|---|---|
| JP | 2011-246431 A | 12/2011 |
| JP | 5622188 B2 | 10/2014 |
| WO | WO 98/02146 A2 | 1/1998 |

\* cited by examiner

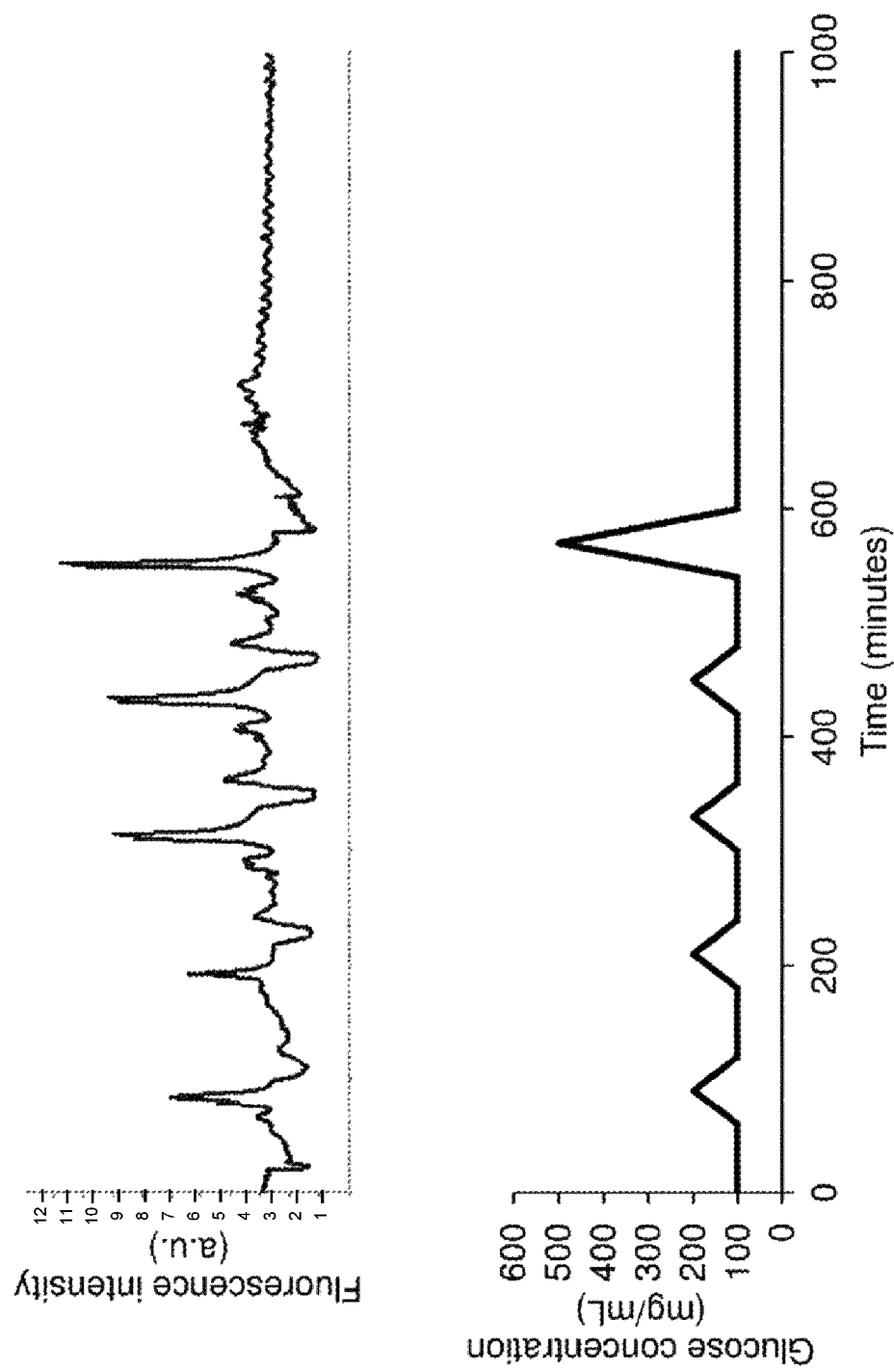

DRUG DELIVERY DEVICE

CROSS-REFERENCE TO RELATED APPLICATIONS

This application is a National Stage application of PCT/JP2016/081407, filed Oct. 24, 2016, which claims priority from Japanese application JP 2015-209192, filed Oct. 23, 2015.

TECHNICAL FIELD

The present invention relates to a drug delivery device. More specifically, the present invention relates to an improved device capable of quickly adjusting the amount of a drug to be delivered depending on stimuli such as blood glucose concentration.

BACKGROUND ART

Diabetes mellitus is characterized by pathologically high glucose concentrations in blood (blood sugar levels). Symptoms of diabetes range from non-subjective symptoms to symptoms leading to disturbance of consciousness. It is known that various complications are caused by diabetes, in addition to symptoms due to hyperglycemia per se.

In vivo blood sugar levels are regulated by several hormones, including insulin. Once the regulation mechanism is impaired, it may lead to the onset of diabetes. Diabetes is roughly classified into type 1 diabetes and type 2 diabetes. Whereas type 1 diabetes is characterized by a small amount of secreted insulin, type 2 diabetes is characterized in that an increase in the blood sugar level cannot be suppressed by a normal amount of secreted insulin due to other factors such as obesity, which results in the development of symptoms.

At present, treatment of diabetes includes the administration of hypoglycemic agents as well as diet therapy and therapeutic exercise. In this regard, insulin therapy is performed as the most effective and safe treatment. This treatment is intended to control the blood sugar level within normal limits by administering a combination of rapid-acting and slow-acting insulin formulations based on blood sugar level monitoring, individual lifestyles, and the like.

Recently, devices that enable patients to administer insulin by themselves, such as pen-type devices, have been developed and widely used. In addition, mainly in Western countries, microcomputer-controlled wearable insulin pumps are spreading. These devices are intended to administer insulin according to a preset algorithm but not to adjust the dosage depending on variations in the actual blood glucose level. Therefore, in the case where the dose of insulin is not appropriate, it might cause hypoglycemia, and the symptoms might be aggravated in some cases. Further, especially in the case of elderly patients and those in need of care, they are expected to often dislike wearing a computer-controlled device. For such reasons, there is a demand for simplified devices.

Meanwhile, the present inventors have developed a gel composition comprising a phenylboronic acid monomer, which is designed to have a reversibly changeable structure depending on the glucose concentration, and have found that the composition is applicable for insulin delivery (Patent Literatures 1 and 2).

CITATION LIST

Patent Literature

Patent Literature 1: JP Patent No. 5622188
Patent Literature 2: JP Patent No. 5696961

SUMMARY OF INVENTION

Technical Problem

The above gel composition expands when the glucose concentration increases while it forms a dehydrated and shrunken layer when the glucose concentration decreases. Therefore, when the blood glucose is in the normal range, gel in the interface in contact with blood becomes plastic-like, thereby achieving suppression of the release of insulin. Patent Literature 2 discloses an insulin administration device which utilizes such property, the device including an indwelling needle having an inner space filled with the above composition. However, there are still some issues to be improved for practical use.

Solution to Problem

The present inventors made various studies to improve a device capable of releasing insulin depending on the glucose concentration and figured out that there is a need for a device which allows a patient to easily use it independently and wear it for at least several days. Then, focusing on the point that the amount of released insulin varies depending on the contact surface area between the gel and the blood, the present inventors examined an increase in the contact surface area in such a device. Consequently, the present inventors have previously developed an insulin delivery device that is configured such that a catheter or needle having a plurality of or a series of openings releases insulin (JP Patent Application No. 2015-096917). A device in such configuration can control the amount of released insulin by adjusting the shape of the opening or the like.

The present inventors have further found that when a device is configured to use a porous body, particularly a hollow fiber having an appropriate molecular weight cut-off, for the entire outer surface, the surface area available for insulin release can be secured in a smaller-size device by a porous body. Further, the present inventors have focused on a finding that insulin can be adequately released by diffusion based on the difference in the insulin concentration between the outside and the inside of gel. In particular, considering that the amount of released insulin decreases as the insulin concentration in the gel decreases, the present inventors have found that insulin can be continuously released by filling a compartment closer to the insulin release portion with a high-concentration insulin solution so as to smoothly supply insulin to the gel. This device can be suitably used for delivering various drugs as well as insulin in an adjustable manner depending on the conditions of the patient.

Specifically, the present invention is described as follows.
[1] A drug delivery device, comprising a porous body having biocompatibility and drug permeability, a stimuli-responsive gel composition filling inside of the porous body, and a drug surrounded by the gel composition inside of the porous body.
[2] The drug delivery device according to [1], wherein the porous body is in the form of a hollow fiber.
[3] The drug delivery device according to [2], wherein the hollow fiber is made of an ultrafiltration membrane, and the ultrafiltration membrane has a molecular weight cut-off of not more than 10,000 daltons.

[4] The drug delivery device according to any one of [1] to [3], wherein the porous body has an outer diameter of 100 to 2,000 µm, an inner diameter of 50 to 1,950 µm, and a length of 0.1 to 100 mm.

[5] A drug delivery device, comprising a biocompatible drug release member having a drug release portion, a stimuli-responsive gel composition filling inside of the drug release member, and a drug surrounded by the gel composition inside of the drug release member, wherein the drug release portion releases the drug by diffusion based on the difference in the drug concentration between the outside and the inside of the gel composition.

[6] The drug delivery device according to any one of [1] to [5], wherein the gel composition is a glucose concentration-responsive gel composition.

[7] The drug delivery device according to [6], wherein the glucose concentration-responsive gel composition is a copolymer gel composition comprising a phenylboronic acid monomer as a monomer.

[8] The drug delivery device according to [7], wherein the copolymer gel composition is formed by polymerizing N-isopropylmethacrylamide (NIPMAAm), a phenylboronic acid monomer (AmECFPBA), and N,N'-methylenebisacrylamide (MBAAm) as a cross-linking agent.

[9] The drug delivery device according to any one of [1] to [8], wherein the drug is insulin.

[10] The drug delivery device according to any one of [1] to [9], wherein the drug is mixed in the gel composition.

[11] The drug delivery device according to any one of [1] to [10], wherein the porous body (or a drug release member) is insertable into the body.

The present description includes part or all of the contents as disclosed in the description and/or drawings of Japanese Patent Application No. 2015-209192, which is a priority document of the present application.

Advantageous Effects of Invention

The drug delivery device of the present invention has a molecular weight cut-off property of functioning in double ways in response to the environment by combining a porous body and a stimuli-responsive gel composition. Alternatively, the device can release a drug by diffusion based on the difference in the drug concentration between the outside and the inside of the gel composition. Therefore, the device can be used very effectively for environment-responsive drug delivery.

The drug delivery device of the present invention also enables effective control of the release of the drug in accordance with the conditions of an individual patient, without using a complicated algorithm.

BRIEF DESCRIPTION OF DRAWINGS

FIG. 1A illustrates an example of a hollow fiber structural body in which the inside of a hollow fiber is filled with gel and the inside of the gel is filled with a drug solution. FIG. 1B illustrates an example of a hollow fiber structural body in which the inside of a hollow fiber is filled with gel containing a drug.

FIG. 4 is a chart of time-dependent changes in the fluorescence intensity of fluorescent modified insulin, which are observed with changes in the glucose concentration outside of the device, in a case where one hollow fiber structural body in FIG. 1A was used as a device.

DESCRIPTION OF EMBODIMENTS

Figure 1:
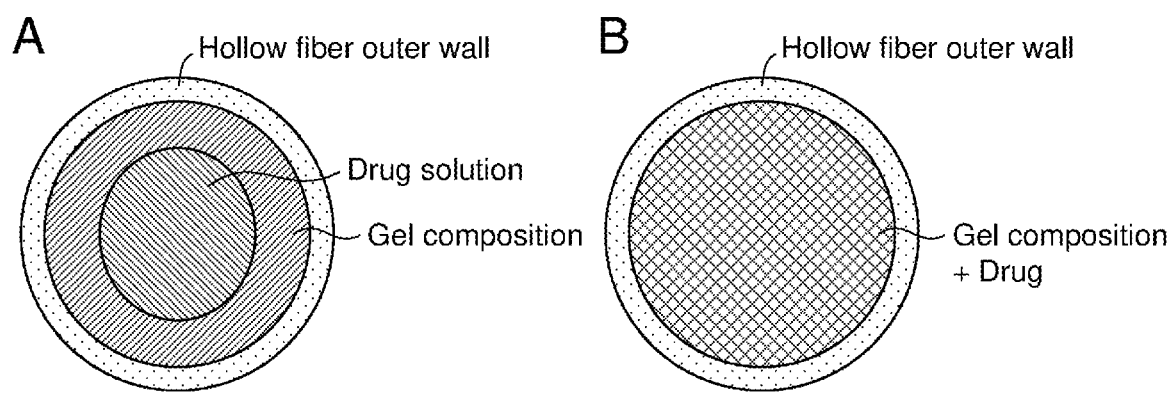
FIG. 1 is a schematic example of a cross-sectional view of the drug delivery device of the present invention.

The present invention is described in detail below.

As described above, in one embodiment, the present invention provides a drug delivery device comprising a porous body having biocompatibility and drug permeability, a stimuli-responsive gel composition filling inside of the porous body, and a drug surrounded by the gel composition inside of the porous body. In another embodiment, the present invention provides a drug delivery device comprising a biocompatible drug release member having a drug release portion, a stimuli-responsive gel composition filling inside of the drug release member, and a drug surrounded by the gel composition inside of the drug release member, wherein the drug release portion releases the drug by diffusion based on the difference in the drug concentration between the outside and the inside of the gel composition.

<Porous Body>

The term "porous body" used herein refers to a substance having a size suitable for insertion into the body and many pores, which preferably includes a hollow fiber having a hollow filamentous structure, and in particular, an ultrafiltration membrane having a molecular weight cut-off which allows transmission of a drug. The term "hollow fiber" is used in the art. Hollow fibers are used for industrial applications such as water purification and the like, pharmaceutical applications for dialysis and the like, and research applications. Hollow fibers having different values of molecular weight cut-off are manufactured depending on the applications and are available. In the case of being used in the device of the present invention, the molecular weight cut-off of the hollow fiber is not particularly limited. However, for the transmission of low molecular drugs, it is preferably several hundred or less, and for the transmission of proteins such as peptides and antibodies, it is preferably approximately 1,000,000 or less. When insulin is used as a drug, the molecular weight cut-off is preferably approximately 10,000 or less.

The porous body material may be any material as long as it has biocompatibility. Examples thereof include, but are not particularly limited to, polysulfone, polyacrylonitrile, cellulose diacetate, cellulose triacetate, polyether sulfone, silicone, polyurethane, polyethylene, Teflon, polyvinyl chloride, silk, and these materials having surface-treated in different ways.

The porous body of the present invention itself can release a drug depending on the difference in the drug concentration between the outside and the inside thereof. Further, in the device of the present invention, the release of a drug is controlled in response to external stimuli of the device, based on characteristics of a gel composition which is present outside of a drug solution or in which the drug is mixed (diffused or dispersed).

The porous body used in the device of the present invention is not particularly limited. In the case of a device used by being inserted into the body, from the viewpoint of suppressing invasiveness, the length of the insertion portion is preferably 10 mm or less, and the outer diameter is preferably approximately 1.2 mm or less. For example, hollow fibers used in dialysis having an outer diameter of approximately 150 to 1,200 µm and an inner diameter of approximately 100 to 1,000 µm are available. Such hollow fibers can be used singly, or a bundle of a plurality of those fibers can be used. The porous body that can be preferably used in the present invention has an outer diameter of 100 to 2,000 µm, an inner diameter of 50 to 1,950 µm, and a length of 0.1 to 100 mm. By using a plurality of porous bodies having smaller outer diameters, it is possible to increase the membrane surface area even in a case where the overall outside diameter remains unchanged. An appropriate porous body can be selected by considering the amount of the drug to be released. In the case of a device that is not inserted into the body, there is no need to consider invasiveness or the like. Therefore, sizes of the porous body such as a length and an outer diameter are not limited, and can be designed appropriately depending on the type of usage.

<Drug Release Member>

The term "drug release member" used herein refers to a member having a hollow structure and a size suitable for insertion into the body, which encompasses, for example, catheters applicable for medical use and needles, microneedle patches, and the like for injection/infusion. Therefore, a drug release member can be used by inserting it into a blood vessel or attaching it on the skin.

<Drug>

A possible drug to be delivered by the device of the present invention is a drug that needs to be delivered under control in accordance with the patient's conditions, and may include low molecular drugs, peptides, and protein pharmaceuticals such as antibodies. Therefore, examples of a drug preferably used include, but are not particularly limited to, antidiabetic agents, such as insulin, which are required to be administered in accordance with the blood glucose concentration.

<Gel Composition>

A gel composition that can be used in the device of the present invention is a composition that has a function to allow permeation of a drug present in a gel composition or a gel composition-filled portion as a result of a change in the degree of swelling in response to external stimuli, for example, depending on pH, light, temperature, metal ions, electric field, magnetic field, a change in the concentration of a chemical substance (such as glucose), redox status, or an antigen-antibody reaction. An example of a stimuli-responsive gel that can be used in the present invention is a glucose concentration-responsive gel composition. Examples of a stimuli-responsive gel that can be used in the present invention include those described in, for example, GELS HANDBOOK (NTS Inc., 1997, mainly edited by Yoshihito Nagata and Kanji Kajiwara).

In the present invention, for example, a mechanism described below, in which the structure of a phenylboronic acid monomer is changed depending on the glucose concentration, can be applied to a preferably usable glucose concentration-responsive gel composition.

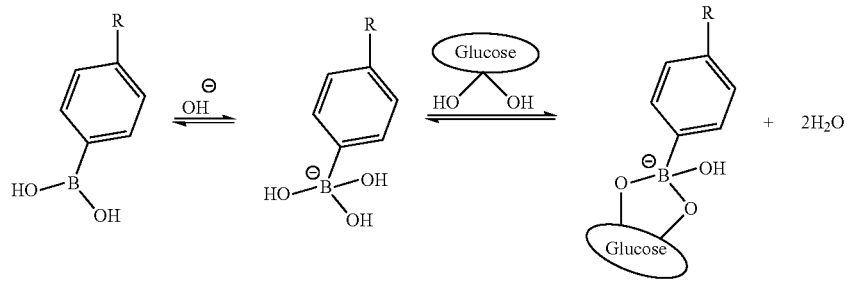

Phenylboronic acid (PBA) dissociated in water can reversibly be linked to a sugar molecule, thereby maintaining the above equilibrium state. When this is combined with a polymer gel having suitable water-solubility, the gel binds thereto as the glucose concentration increases, which results in expansion of the volume while the gel shrinks as the glucose concentration decreases. In a state in which the drug delivery device of the present invention is filled with such gel, the reaction occurs in the gel interface in contact with the blood such that the gel shrinks only in the interface, which results in the formation of a dehydrated shrunken layer that is referred to as a "skin layer" by the present inventors. The device of the present invention utilizes this property for controlled release of a drug.

A gel composition that is suitably usable to fill the drug delivery device of the present invention is a copolymer gel composition comprising a phenylboronic acid monomer having the above properties as a monomer. Examples thereof include, but are not particularly limited to, those described in Patent Literatures 1 and 2.

A phenylboronic acid monomer used for the preparation of a gel composition according to the invention is represented by, but is not limited to, for example, the following formula.

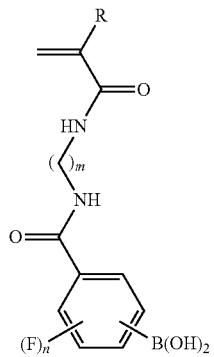

(where R is H or $CH_3$, F is independently present, n is 1, 2, 3 or 4, and m is 0 or an integer of 1 or more.)

The above phenylboronic acid monomer has a structure in which a hydrogen atom on the phenyl ring has a fluorinated phenylboronic acid group substituted with 1 to 4 fluorine atoms, and a carbon atom of the amide group is bound to the phenyl ring. The phenylboronic acid monomer having the above structure has high hydrophilicity, and since the phenyl ring is fluorinated, its pKa can be controlled to 7.4 or less in the physiological level. Further, this phenylboronic acid monomer has the abilities not only to recognize a sugar in a physiological environment but also to copolymerize with a gelling agent or a cross-linking agent described below via an unsaturated bond. Thus, it is possible for the monomer to form a gel that causes a phase change depending on the glucose concentration.

In the phenylboronic acid monomer described above, in a case where one hydrogen on the phenyl ring is substituted with a fluorine atom, F and $B(OH)_2$ may be introduced at any of ortho, meta, and para positions.

In general, when m is 1 or more, the pKa of the phenylboronic acid monomer can be controlled to a lower value than that of the phenylboronic acid monomer when m is 0.

One example of the phenylboronic acid monomer is a phenylboronic acid monomer for which n is 1 and m is 2, which is 4-(2-acrylamideethylcarbamoyl)-3-fluorophenyl-boronic acid (AmECFPBA) as a particularly preferable phenylboronic acid monomer.

The gel composition can be prepared from a gelling agent having a property that does not cause toxic or harmful effects to the biological functions in the body (biocompatibility), the above phenylboronic acid monomer, and a cross-linking agent. A method for preparing the gel composition is not particularly limited. However, it can be prepared by mixing a gelling agent and a phenylboronic acid monomer, which form the backbone of gel, and a cross-linking agent at a predetermined molar mixing ratio to induce a polymerization reaction. For polymerization, a polymerization initiator is used, if necessary.

It is preferable for the drug delivery device of the present invention to preliminarily contain a drug in the gel composition. For such purpose, the drug may be diffused in the gel by immersing the gel in an aqueous solution such as a phosphate buffer solution containing the drug at a predetermined concentration. Then, by immersing the gel removed from the solution in, for example, hydrochloric acid so as to form a thin dehydrated shrunken layer on the surface of the gel body (referred to as a "skin layer"), a gel encapsulating (loading) the drug, which can be filled into the device, can be obtained.

The gelling agent, the phenylboronic acid monomer, and the cross-linking agent may be mixed at a favorable ratio which results in a composition that enables controlling the release of a drug depending on the glucose concentration under physiological conditions. The ratio may vary depending on the monomer employed and thus is not particularly limited. The present inventors have already prepared gel by combining various types of phenylboronic acid monomers with a gelling agent and a cross-linking agent at different ratios and examined behaviors of each obtained gel (see, for example, JP Patent No. 5622188). A person skilled in the art could obtain gel having a favorable composition based on the description in the present application and the technical information reported in the art.

An example of the gel composition preferably used in the present invention is a composition for which the molar mixing ratio of a gelling agent (or backbone):a phenylboronic acid monomer:a cross-linking agent is adjusted to 91.5:7.5:1. However, the present invention is not limited thereto. Gel may be prepared by adjusting the molar mixing ratio of a gelling agent:a phenylboronic acid monomer:a cross-linking agent as long as a gel body formed with a composition comprising a gelling agent, a phenylboronic acid monomer, and a cross-linking agent can expand or shrink in response to the glucose concentration, it can maintain the property of having PKa of 7.4 or less, and it can be formed into gel.

The gelling agent may be a biocompatible material which has biocompatibility and can gelate, for example, may include acrylamide gelling agent having biocompatibility. Specific examples thereof include N-isopropylmethacrylamide (NIPMAAm), N-isopropylacrylamide (NIPAAm), and N,N-diethylacrylamide (DMAAm).

The cross-linking agent may also be a biocompatible substance capable of cross-linking monomers. Examples thereof include N,N'-methylenebisacrylamide (MBAAm), ethyleneglycoldimethacrylate (EGDMA), N,N'-methylenebismethacrylamide (MBMAAm), and other various cross-linking agents.

Thus, in one preferred embodiment of the present invention, the gel composition is prepared by polymerizing N-isopropylmethacrylamide (NIPMAAm), 4-(2 acrylamido-ethylcarbamoyl)-3-fluorophenylboronic acid (AmECFPBA), and N,N'-methylenebisacrylamide (MBAAm) at a molar mixing ratio of 91.5:7.5:1 (mol %) as shown below.

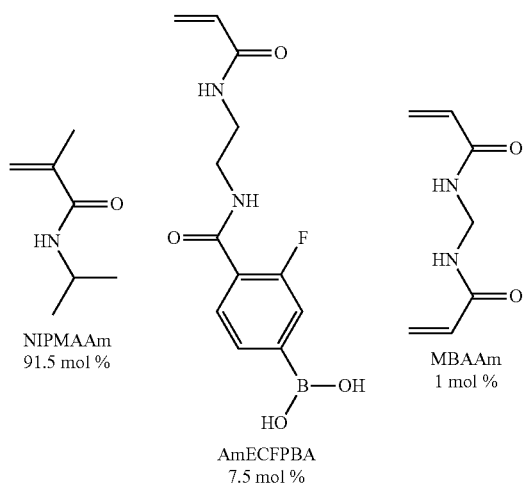

In the above gel composition, a phenylboronic acid monomer is copolymerized with a gelling agent, thereby forming a gel body. This gel can be configured such that a drug is diffused therein and the surface of the gel body is surrounded by a dehydrated shrunken layer. In this manner, under physiological conditions including pKa of 7.4 or less and a temperature of 35° C. to 40° C., when the glucose concentration increases, expansion of the gel causes the dehydrated shrunken layer to disappear, thereby allowing the drug in the gel to be released outside of the gel.

Meanwhile, when the glucose concentration decreases again, the expanded gel shrinks such that the dehydrated and shrunken layer (skin layer) is formed again over the entire surface of the gel, thereby preventing the drug in the gel from being released outside of the gel.

Thus, the gel composition used in the present invention can autonomously release the drug in response to the glucose concentration.

<Device>

The configuration of the drug delivery device of the present invention is more specifically described with reference to the drawings.

FIG. 1 is a schematic example of a cross-sectional view of the drug delivery device of the present invention using a porous body. In FIG. 1A, a hollow fiber is used as a porous body, a gel composition fills the hollow fiber along the inner wall thereof, and a drug solution fills inside of the gel composition. However, in accordance with the method for manufacturing the device, and since the device is configured to be used in vivo, gel may be present in pores of the outer wall of the hollow fiber. Further, it is also possible to form a plurality of compartments with the gel composition or the like. In such case, it is preferable to configure the device such that a high-concentration drug solution is present in a compartment near the hollow fiber outer wall.

FIG. 1B illustrates an example in which the inside of the hollow fiber structure is uniformly filled with a gel composition containing a drug. In such configuration, the gel composition may be present also in pores of the hollow fiber outer wall. It is preferable to allow a high-concentration drug to be present in a compartment close to the hollow fiber outer wall by adjusting the gel composition, the content of the drug, and the like.

The device of the present invention may have, but is not limited to, a configuration in which the device is formed using one hollow fiber or 2 to 100,000 hollow fibers having the above structure. The hollow fiber structure may have both ends in a closed form, but it is not limited thereto, since the state of the gel composition for filling and the release of the drug from the gel composition are adjustable for the device of the present invention.

The device of the present invention may include a reservoir such that a drug can be supplied after the drug is released from the porous body (hollow fiber) or the drug release member (drug release portion). A reservoir for the hollow fiber may be in the form of, for example, a catheter having an outer diameter of 1 mm to 2 mm and a length of 10 mm to 200 mm. A commercially available silicon catheter having a size of 4 Fr (inner diameter: 0.6 mm/outer diameter:1.2 mm). The reservoir, if present, may be filled with approximately 10 ml to 30 ml of a drug solution for supplementation, and connected to an open end of the hollow fiber structure or an opening formed on the drug release member, thereby allowing continuously controlled release of the drug during a desired period of insertion or attachment. However, as long as the required amount of the drug to be delivered during a predetermined period can be retained, it is not always necessary to provide the reservoir.

Figure 2A:
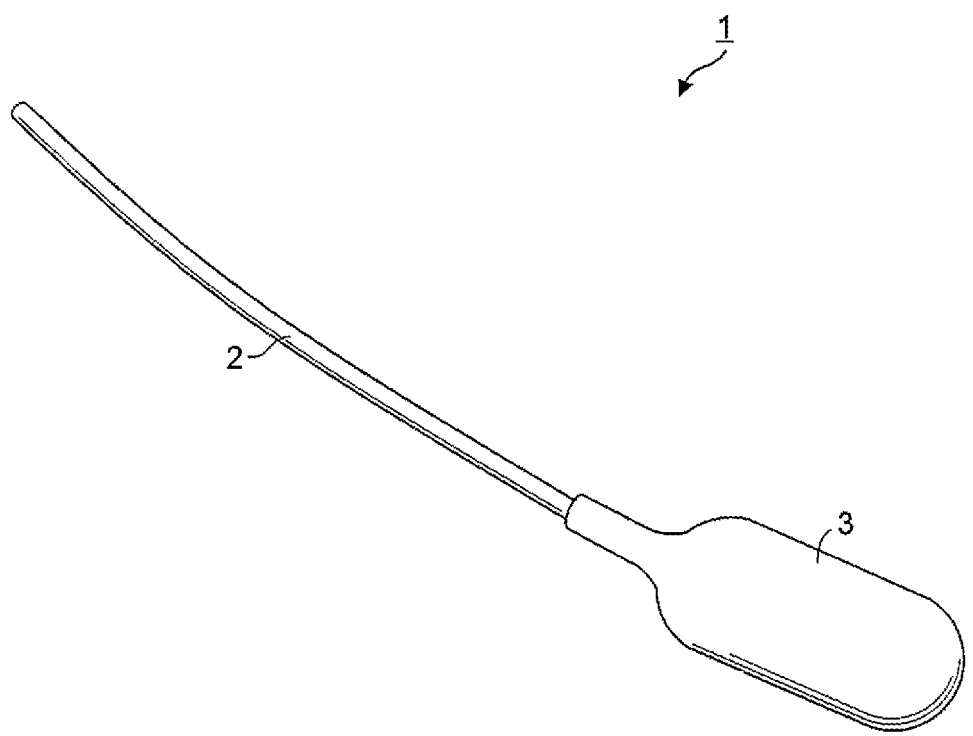
FIG. 2A is another schematic example of the structure of the drug delivery device of the present invention. A device 1 includes a catheter 2 and a reservoir 3, and side holes are formed on the catheter 2.
Figure 2B:
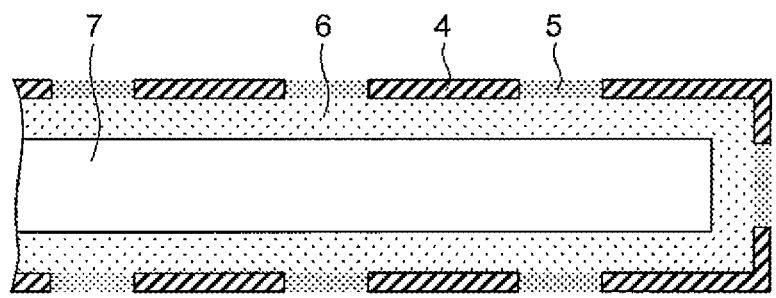
FIG. 2B is an enlarged view of the catheter in FIG. 2A. A plurality of side holes 5 are formed on a catheter side wall 4. A gel-filled portion 6 is formed inside along the inner wall of the catheter, and a drug-filled portion 7 is provided in a hollow space which is not filled with gel.

FIG. 2A illustrates an example of the appearance of the device in another embodiment of the present invention. In this configuration, a device 1 includes, as drug release members, a catheter 2 and a reservoir 3. The catheter 2 is in the form of a tube having, for example, an outer diameter of 1 mm to 2 mm and a length of 10 mm to 200 mm, preferably 15 mm to 200 mm, and more preferably 20 mm to 200 mm. A commercially available silicon catheter having a size of 4 Fr can be suitably used. As illustrated in FIG. 2B, the catheter may have a plurality of side holes 5 as drug release portions on a side wall 4. Side holes may also be present at the tip of the catheter regardless of the expression "side." A gel-filled portion 6, in which a copolymer gel composition comprising a phenylboronic acid monomer as a monomer is present, is provided along the inner wall of the catheter. A drug-filled portion 7 is provided such that it is surrounded by the gel-filled portion 6. One feature of the device in this embodiment is that the drug-filled portion 7 is present in a compartment surrounded by the gel-filled portion 6, thereby making it possible to fill a higher concentration drug in a compartment closer to the drug release portion. The thickness of the gel-filled portion 6 may be in a range of 10 to 500 μm in the catheter, thereby enabling controlled release of a drug (insulin) depending on the glucose concentration.

The reservoir 3 is provided such that a drug can be refilled in the drug-filled portion 7. Thus, it is possible to fill the drug-filled portion of the catheter and the reservoir with a drug in a total volume of up to approximately 10 ml, thereby enabling continuously controlled release of the drug during a desired period of insertion or attachment.

Figure 2C:
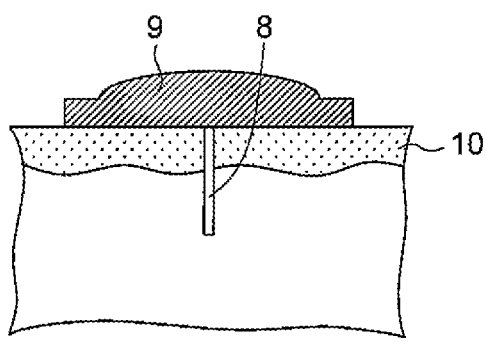
FIG. 2C is another schematic example of the structure of the drug delivery device of the present invention. The device includes a needle 8 and a reservoir 9, and side holes are formed on the needle 8. This device has a structure that is applicable for use being attached on the skin 10.

FIG. 2C illustrates yet another embodiment of the device of the present invention. This device is composed of a needle 8 as a drug release member and a reservoir 9. In this configuration, the device can be used in the form of being attached on the skin 10. The needle 8 may have, for example, an outer diameter of 0.5 to 1 mm and a length of 1 mm to 20 mm and preferably 5 mm to 10 mm. A commercially available silicon catheter with a size of 4 Fr may be suitably used, or a metal needle may also be used. Further, a plurality of needles 8 can be employed for one reservoir 9. The drug release portion provided to the needle 8 may be plurally formed on the tip, a side, or the like of the needle. In such embodiment, the needle 8 can be configured such that it penetrates the skin so as to reach the subcutaneous tissue or into the blood vessel, thereby releasing the drug. In this embodiment, a spring or the like may be provided inside of the reservoir in order to prevent the reservoir 9 from being broken due to external pressure. The device of this embodiment can be used by a patient himself/herself according to a physician's instructions, similarly as a currently available pen-type or patch-type device.

In yet another embodiment of the device of the present invention, the drug release member may be a microneedle patch instead of a needle illustrated in FIG. 2C. A microneedle patch is a sheet-type patch comprising a biocompatible polymer as a material, for example, which is formed with many protrusions of 150 µm to 2000 µm in length (drug release portions). The drug is allowed to permeate through the skin via the protrusions by applying the patch on the skin surface, thereby allowing the drug to be efficiently delivered into the body. Since the protrusions are finely formed, they do not cause pain when the patch is applied on the skin.

Materials used for the drug release member of the present invention may be any materials suitable for insertion into the body. Examples thereof include, but are not particularly limited to: silicone, polyurethane, polyethylene, Teflon, polyvinyl chloride, silk, and these materials having surface-treated in different ways; and metals such as titanium, stainless steel, tantalum, cobalt alloy, and nickel-titanium alloy (e.g., nitinol). In the case of using silicone or the like, it is preferable to immobilize gel by binding the gel with the device via, for example, a silane coupling. Further, in order to prevent adhesion of various proteins, fat, and the like present in the body to the device and clogging due to such substances, the openings (e.g. side holes 5) or the device as a whole can be coated with a polymer such as a PEG (polyethylene glycol) polymer. An example of a preferable polymer having biocompatibility is tetra-branched Tetra-PEG gel that is a high-strength gel having a network formed with polyethylene glycol (see, e.g., Macromolecules, 2008, 41(14), pp. 5379-5384; Macromolecules, 2009, 42(4), pp. 1344-1351), which is commercially available as SUN-BRIGHT series (manufactured by NOF Corporation). For example, Tetra-PEG gel, which can be obtained by mixing and reacting a terminal amino group-modified Tetra-PEG having a molecular weight of approximately 10,000 and a terminal active ester group-modified Tetra-PEG having a molecular weight of approximately 10,000, allows permeation of insulin (molecular weight: approximately 6,000) and glucose (molecular weight: approximately 180) while it does not allow permeation of proteins having greater molecular weights. Accordingly, such polymer does not inhibit the contact between glucose and the gel or the release of insulin from the gel while preventing the adhesion of proteins and the like The above purpose can be achieved by coating the drug release portion of the device where gel is exposed and, if necessary, the surface of the drug release member of the device with Tetra-PEG. The step of coating with Tetra-PEG can be carried out after the completion of the device or after filling of the gel composition in the gel-filled portion 6.

Figure 3A:
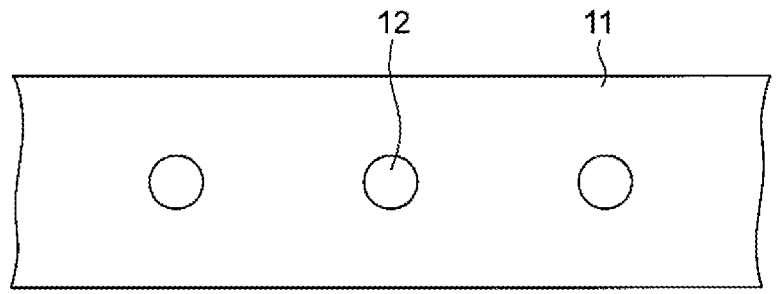
FIG. 3A is an enlarged view of a catheter 11 on which a plurality of circular side holes 12 are formed.
Figure 3B:
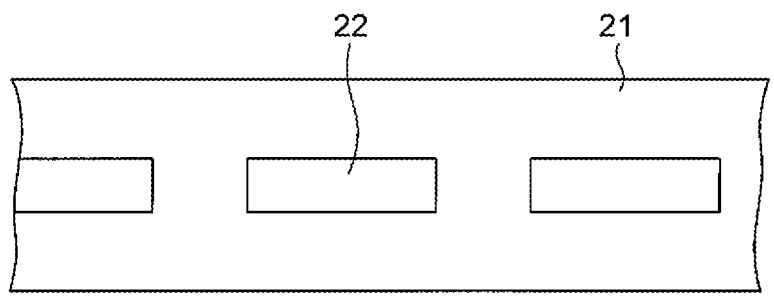
FIG. 3B is an enlarged view of a catheter 21 on which a plurality of slit-like side holes 22 are formed.
Figure 3C:
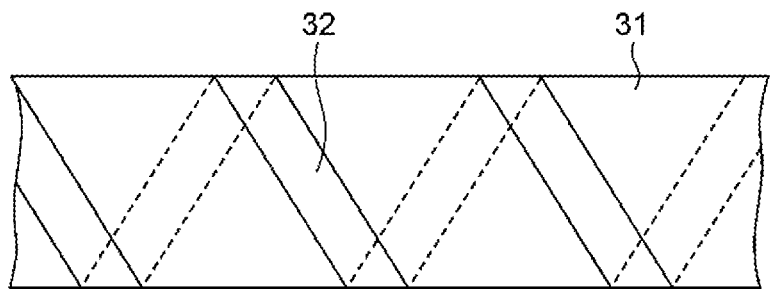
FIG. 3C is an enlarged view of a catheter 31 on which an opening 32 is continuously formed in a spiral manner.

The catheter, needle, microneedle patch, and the like, which are drug release members of the present invention, has a drug release portion. The drug release portion releases a drug by diffusion depending on the difference in the drug concentration between the outside and the inside of the gel composition. For this purpose, the shape and number of drug release portions may be selected. The shape of drug release portions is not particularly limited as long as such release can be achieved. For example, as illustrated in FIGS. 3A and 3B, side holes may be in an arbitrary shape such as a circular, oval, or slit shape. The number of drug release portions is not limited as well. For example, in the case of a catheter, 10 to 100 circular side holes (drug release portions) having the diameter of 300 µm may be formed at 1-mm intervals. Alternatively, as illustrated in FIG. 3C, the drug release portions may be formed by perforating a side wall of the catheter (or needle or each protrusion of a microneedle patch) in a spiral manner. In this case, if there is concern that the structure of the catheter itself becomes weak, a support structure made of a metal, a polymer, or the like may be provided inside of the catheter. The surface area of the device in contact with blood or the like may be variable depending on the design of the drug release portion within a range of approximately 1% to 99% with respect to the entire surface area of the device.

The device of the present invention may preferably be inserted into the body of a patient. Alternatively, the device may be attached to a suitable external part of the patient's body in the form of, for example, a pen-type or tube-type device, that can be used for dialysis, if necessary.

With the above structure, the device of the present invention can be used preferably in a state of being inserted into the patient's body, for example, for approximately several days to 1 week so as to continuously release a drug such as insulin depending on each patient's blood sugar level, for example. It is preferable to adjust the amount of insulin to be released such that, the blood insulin concentration falls within a range of, for example, 70 to 140 mg/dL. Further, particularly in the case of providing a reservoir, it is preferable to provide means of preventing a back flow such as a check valve so shat a drug does not flow back from the body side.

In the device of the present invention, the gel composition causes phase transition in response to stimuli. For example, in the case of a gel composition comprising a phenylboronic acid monomer, phase transition is induced depending on a predetermined specific threshold. Thus, the device can respond to variations in the blood sugar level of an individual patient and continuously control the release of a drug such as insulin in a state of being attached to the patient, without using complicated algorithm.

The hypoglycemic state varies depending on the patient, and the amount of a drug to be delivered may also vary depending on the patient. In order to adjust the amount of a drug to be delivered, the concentration of a drug to be filled inside of a device can be adjusted (for example, by employing the concentration suitable for the patient or higher concentration on the drug release side), in addition to the adjustment of the size or number of pores in the porous body (in the case of hollow fibers, adjustment of membrane surface), and the shape or number of drug release portions formed on the drug release member. Further, rapid-acting, intermediate-acting, and long-acting preparations are available as insulin formulations, and a device further suitable for an individual patient can be provided by appropriately selecting such preparations.

EXAMPLES

The present invention is specifically described with reference to the Examples below. However, the present invention is not limited to these Examples.

Example 1

N-isopropylmethacrylamide (NIPMAAm) and a phenylboronic acid monomer (AmECFPBA) as gelling agents (i.e., backbone), N,N'-methylenebisacrylamide (MBAAm) as a cross-linking agent, and 2,2'-azobisisobutyronitrile as a polymerization initiator were mixed at a molar mixing ratio of 91.5:7.5:1:0.1 and subjected to radical polymerization in a capillary having a diameter of 1 mm, to prepare a gel.

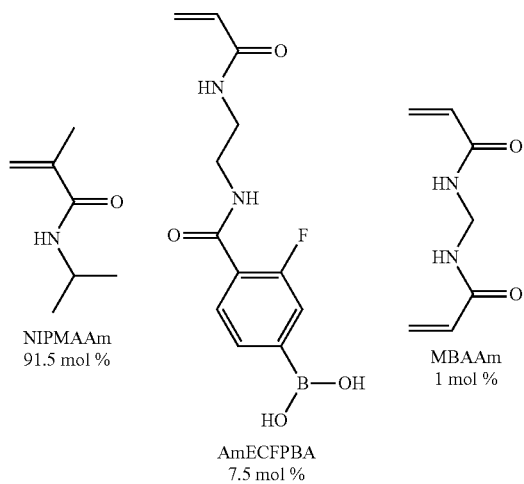

The obtained gel was allowed to swell in a solution of a human insulin preparation (Humulin R injection manufactured by Eli Lilly and Company) or PBS at room temperature and then immersed in a 0.1 M hydrochloric acid aqueous solution at 37° C. for 1 hour, thereby encapsulating insulin.

The gel was capable of inducing phase transition with a normoglycemia (1 g/L) as a threshold under physiological conditions (pH 7.4, 37° C.). Controlled release of insulin was confirmed in a control mode of a skin layer generated on the gel surface. In other words, it was confirmed that no insulin was released at glucose concentrations within a range of normal blood sugar levels, while rapid release of insulin occurred in the presence of high-concentration glucose, indicating that insulin was released depending on the glucose concentration (data not shown). It was also confirmed that physiological activity of insulin inside of the gel or insulin released from the gel was maintained upon encapsulation in the gel and during the subsequent retention for not less than 72 hours.

Example 2

One of hollow fibers used in the polysulfone dialyzer manufactured by Asahi Kasei Medical Co., Ltd. (APS-15SA 4537693003682) was used as a device (inner diameter: 185 μm; thickness: 45 μm). In this Example, a commercially available silicon catheter for humans (4 Fr: inner diameter of about 600 μm; Prime Tech Co., Ltd.) was connected to the device and allowed to function as a reservoir for supplying insulin.

An insulin release experiment was conducted using a high performance liquid chromatography (HPLC) system (JASCO, Japan) equipped with two pumps and an internal detector for refractive index (RI), UV, and fluorescence intensity detection.

Gel prepared in the same manner as in Example 1 was immersed in PBS containing 130 mg/L FITC-labeled bovine insulin (WAKO, Japan) at 4° C. for 24 hours, thereby encapsulating FITC-labeled insulin in the gel. Then, the device of the present invention was filled with the gel. The device was immediately placed in a 0.01 M HCl aqueous solution and incubated at 37° C. for 60 minutes, thereby forming a skin layer on the gel surface.

A Tricorn Empty High-Performance Column (GE Healthcare, USA) having an inner diameter of 10 mm and a length of 50 mm was loaded with the device containing insulin and the gel of this Example. The column was placed in a constant temperature flow (37° C.) of PBS (pH 7.4, I=0.15) containing 1 g/L glucose, and connected to the HPLC system while the flow rate in the chamber was maintained at 1 mL/minute. Thereafter, an equilibrium state, in which leakage of insulin bound to the gel surface was not observed, was achieved in 2 to 3 hours.

The amount of FITC-labeled insulin released from the gel was determined by monitoring the 520 nm fluorescence intensity (excitation wavelength: 495 nm) in the solution. PBS containing 10 g/L glucose and PBS free of glucose were prepared and supplied by the two pumps of the system according to the program. The solutions supplied from the pumps were continuously mixed in a mixer unit, thereby achieving a predetermined glucose concentration gradient pattern (0 to 5 g/L). The in situ glucose concentration during the experiment was monitored by an RI detector in a downstream portion adjacent to the column.

As a result, as indicated in FIG. 4, it was confirmed that the fluorescence intensity increased as the glucose concentration in fluid outside of the hollow fiber increased, suggesting that insulin was released from the device. When the glucose concentration declined, the release of insulin was suppressed.

Example 3

The same system as in Example 2 was used, a device was prepared by closing both ends of 10 hollow fibers used in a polysulfone dialyzer (APS-15SA 4537693003682) manufactured by Asahi Kasei Medical Co., Ltd. No reservoir was used in the configuration of this Example.

Figure 5:
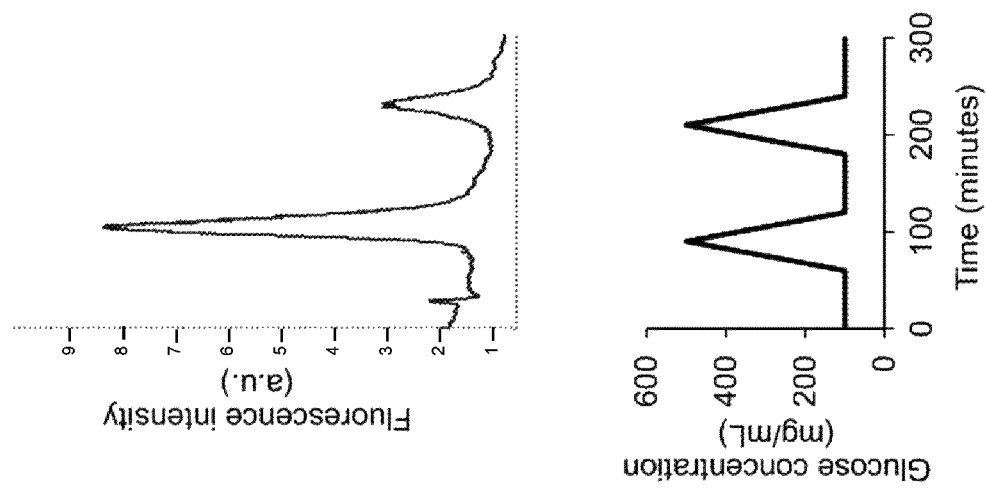
FIG. 5 is a chart of time-dependent changes in the fluorescence intensity of fluorescent modified insulin, which are observed with changes in the glucose concentration outside of the device, in a case where ten hollow fiber structural bodies in FIG. 1A were used as a bundle-type device.

As a result, as indicated in FIG. 5, it was confirmed that the fluorescence intensity increased as the glucose concentration in fluid outside of the hollow fiber increased, suggesting that insulin was released from the device. When the glucose concentration declined, the release of insulin was suppressed.

Example 4

The same system as in Example 2 was used with a hollow fiber (polyacrylonitrile; inner diameter: 800 μm; length: 130 mm) used in MICROZA (AHP-0013 D) manufactured Asahi Kasei Chemicals Corporation, which was employed as a device. No reservoir was used in the configuration of this Example.

Figure 6:
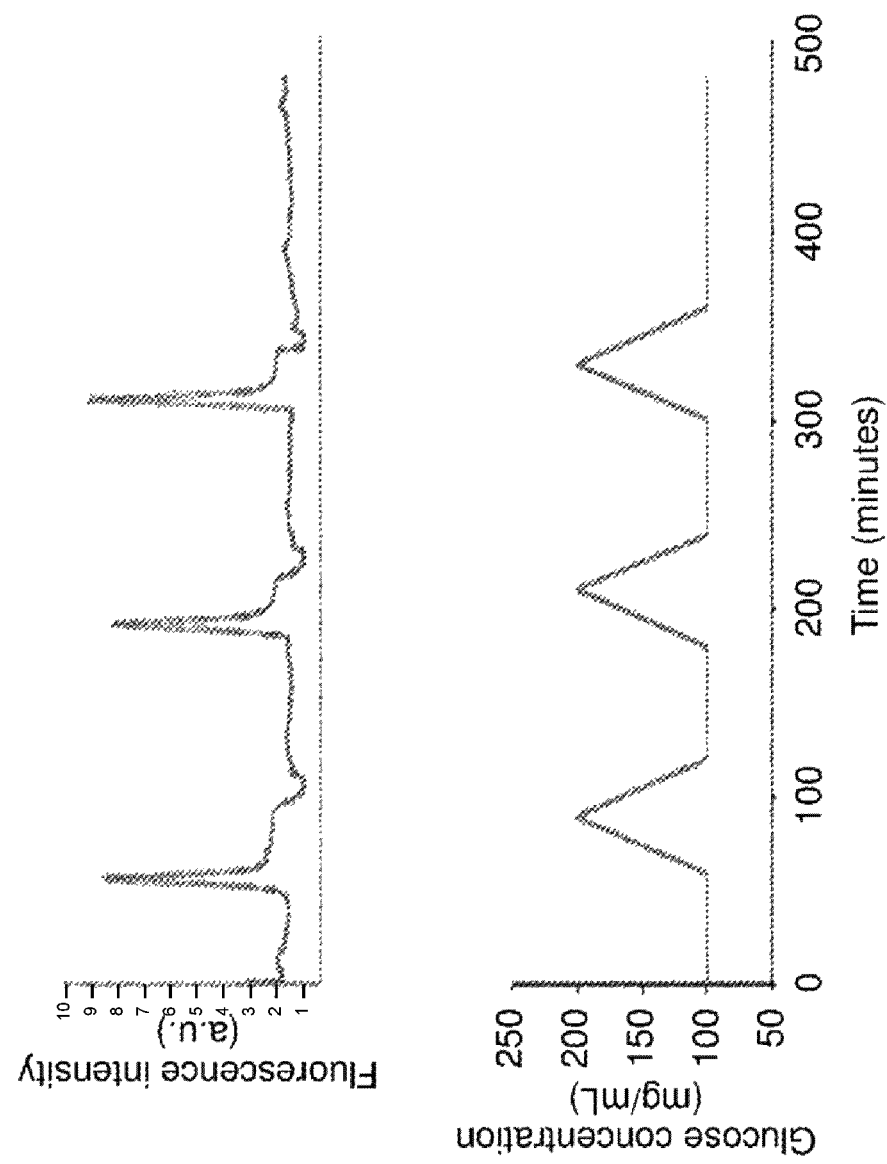
FIG. 6 is a chart of time-dependent changes in the fluorescence intensity of fluorescent modified insulin, which are observed with changes in the glucose concentration outside of the device, in a case where a hollow fiber structural body in FIG. 1B was used as a device.

As a result, as indicated in FIG. 6, it was confirmed that the fluorescence intensity increased as the glucose concentration in fluid outside of the hollow fiber increased, suggesting that insulin was released from the device. When the glucose concentration declined, the release of insulin was suppressed.

Example 5

AKITA mice (7 weeks old, Japan SLC, Inc.), which are type 2 diabetes model animals, were used for confirming the effects of the device of the present invention illustrated in FIGS. 2A and 2B.

A commercially available silicon catheter for humans (4. Fr; inner diameter: approximately 600 μm; Prime Tech Co., Ltd.) was used as a drug release member, and through holes having a diameter of 300 μm serving as drug release portions (side holes) were formed thereon by laser processing. In order to confirm whether or not the number of side holes would cause differences in the effects, three types of devices having 12 holes (#1), 24 holes (#2), and 48 holes (#4) were prepared. After washing, a methacryloyl group was introduced by silane coupling agent treatment, and the gel prepared in Example 1 was applied to the catheter inner wall. At that time, aluminum wire having a diameter of 300 μm was allowed to indwell as a template in the central axial region of each catheter and removed the wire after gelation reaction, thereby forming a hollow structure. After washing with water and sterilization treatment in an autoclave, the hollow portion of each device was filled with an insulin preparation for humans (Humulin R injection), and both ends thereof were closed. In the control group, gel swollen in PBS was introduced and the hollow portion was filled with PBS. The length of the catheter portion was set to 20 cm, and each catheter was surgically implanted subcutaneously in each mouse.

The three types of devices of Example 5 were surgically embedded subcutaneously into AKITA mice (5 mice in each group). Blood sugar levels were measured using a commercially available glucose sensor (Glutest Sensor, Sanwa Chemical Co., Ltd.) 48 hours after embedment. The number of side holes in the control group was set to 24.

Figure 7:
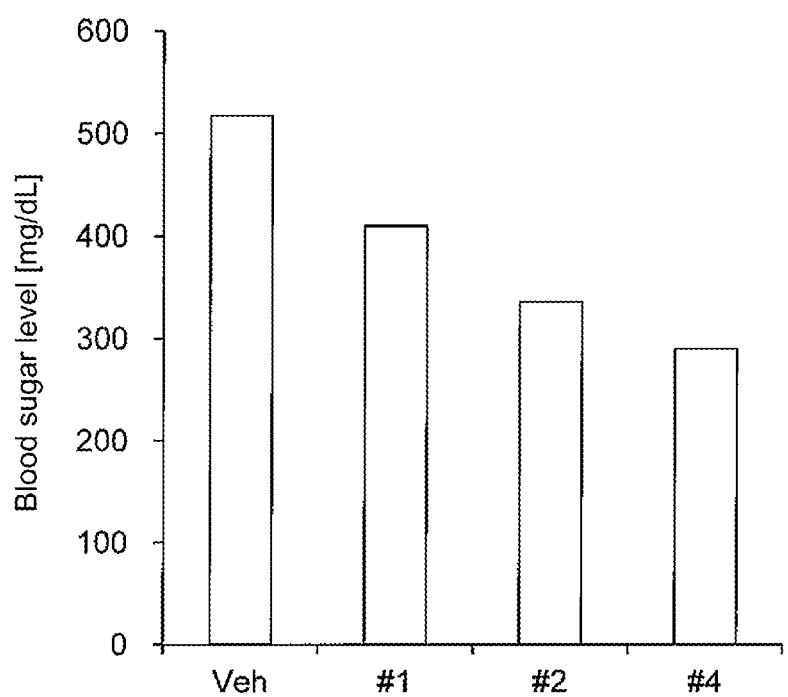
FIG. 7 is a chart showing the effect of suppressing blood sugar levels in AKITA mice 48 hours after subcutaneous implantation of the drug delivery device in FIG. 2A: Veh: control (no insulin), : #1: the number of side holes 12; #2: the number of side holes 24; #4: the number of side holes 48.

As a result, as compared to the control group, in mice using the devices of Example 5 filled with insulin, their blood sugar levels decreased after 48 hours. It was confirmed that this effect was intensified as the number of side holes increased (FIG. 7).

Figure 8:
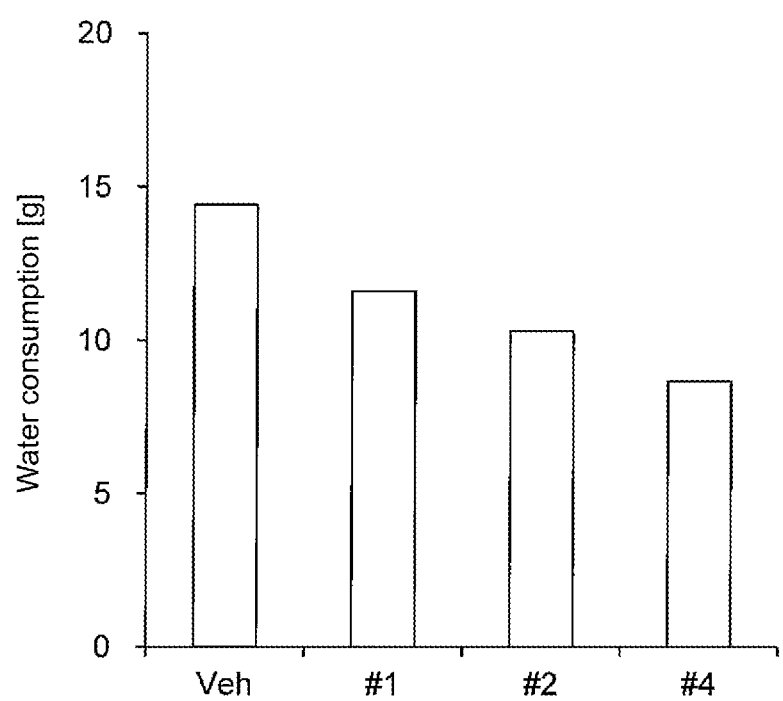
FIG. 8 is a chart showing the effect of suppressing water consumption in AKITA mice 48 hours after subcutaneous implantation of the drug delivery device in FIG. 2A: Veh: control (no insulin): #1: the number of side holes 12; #2: the number of side holes 24; #4: the number of side holes 48.

Further, the water consumption was determined for 24 hours from 24 hours to 48 hours after the device implantation using the same test and control groups. As a result, compared to the control group, each mouse using the device of the present invention filled with insulin showed a decrease in the water consumption. It was confirmed that this effect was also intensified as the number of side holes increased (FIG. 8).

Example 6

A silicon catheter device having 24 side holes was prepared in the same manner as in Example 5. In this Example, each device was filled with high-concentration insulin (22.5 mg/ml), low-concentration insulin (3.5 mg/ml), or PBS.

The obtained device was surgically embedded subcutaneously into healthy mice (9 weeks old, C57BL/6J), and time-dependent changes in the blood sugar level were observed using a glucose sensor.

Specifically, the blood sugar level was observed for 3 days after implantation of the device, and it was confirmed that the blood sugar level was maintained at almost normal levels. Thereafter, although every mouse showed mild hypoglycemia (50-70 mg/dL) due to fasting for 16 hours, there was no significant difference between the test group using the device of the present invention filled with insulin, and the control group using the device filled with PBS. Therefore, safety of the device was confirmed.

Figure 9:
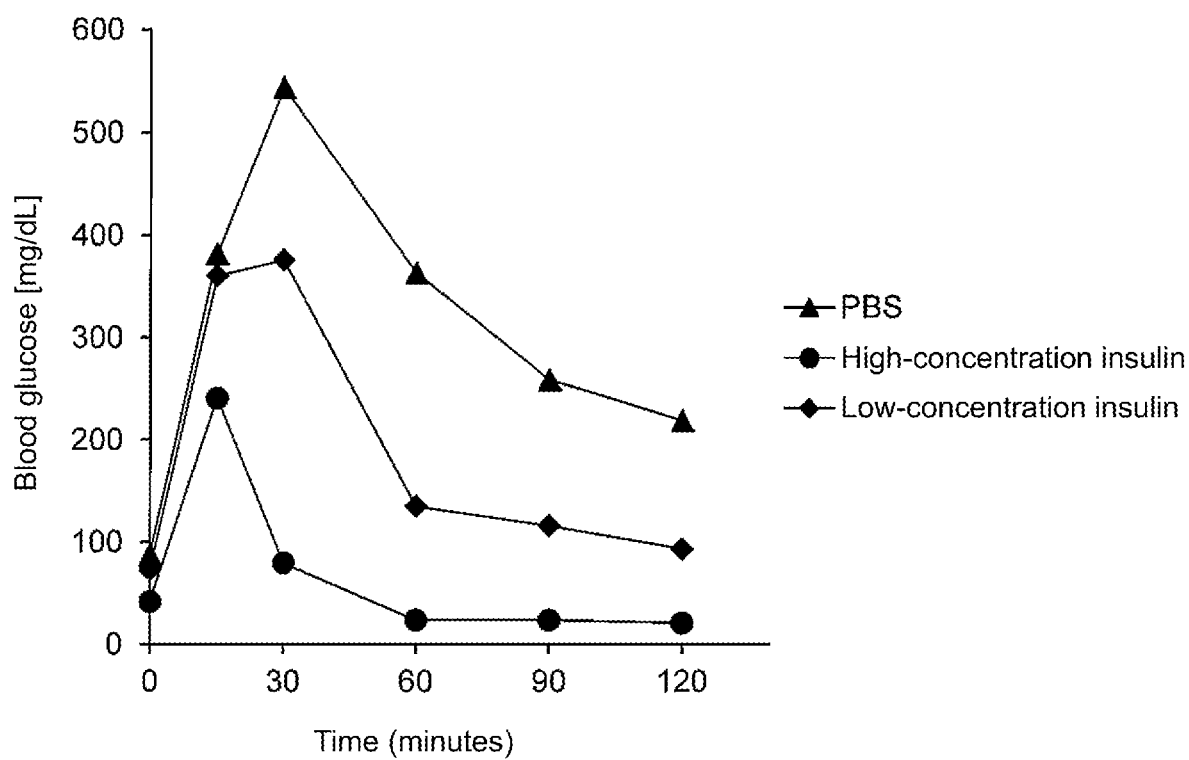
FIG. 9 is a chart showing the effect of suppressing blood sugar levels in healthy mice, into which the drug delivery device in FIG. 2A filled with high-concentration insulin (22.5 mg/ml), low-concentration insulin (3.5 mg/ml) or PBS, was subcutaneously implanted.

Next, glucose was administered intraperitoneally at a dose of 3 mg/g body weight for acute glucose loading. As a result, an increase in the blood sugar level in the insulin delivery device group was remarkably suppressed as compared to the control group. Thus, the responsiveness of the device to rapid blood glucose variations was confirmed (FIG. 9).

Example 7

Figure 10A:
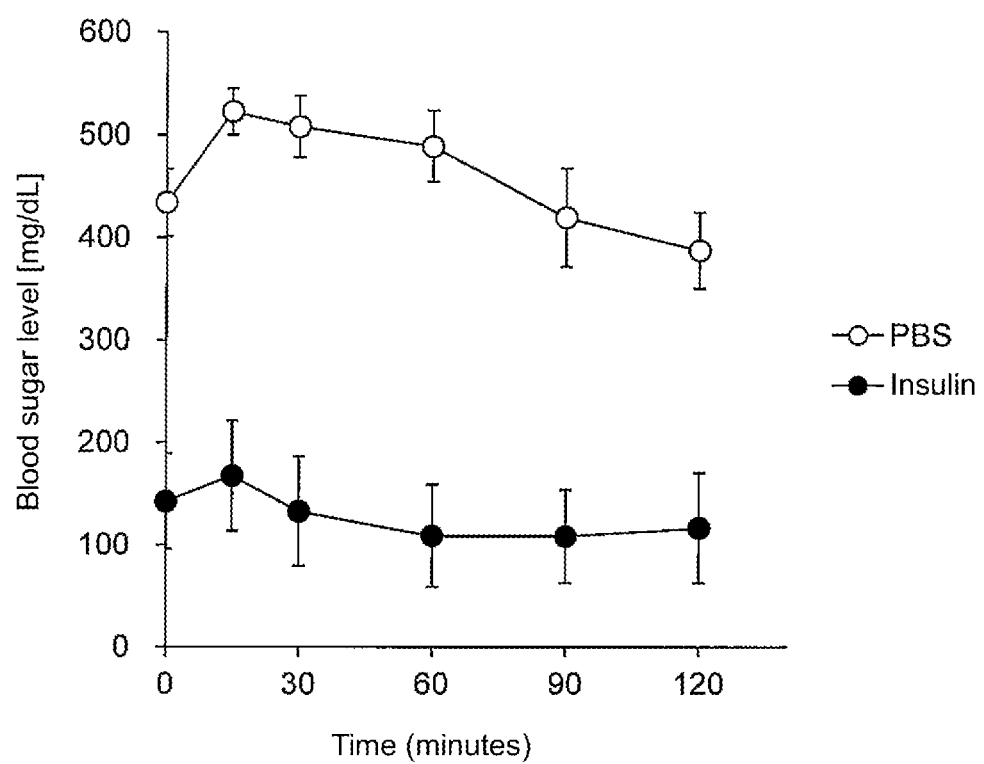
FIG. 10A is a chart showing the effect of suppressing blood sugar levels in STZ-induced type 1 diabetes model mice, into which the drug delivery device in FIG. 2A filled with insulin or PBS was subcutaneously implanted.

Streptozocin (STZ)-induced type 1 diabetes model mice (9 weeks old, C57BL/6J) were tested in the same manner as in Example 6. In this Example, the device was filled with insulin (3.6 mg/ml) or PBS. High blood sugar levels in the mice were maintained even after fasting for 16 hours. Although substantially no decrease in the blood sugar level was observed in the control group using the device filled with PBS, a significant decrease in the blood sugar level was observed in in the insulin delivery device group, and the effect lasted for 120 minutes (FIG. 10A).

Figure 10B:
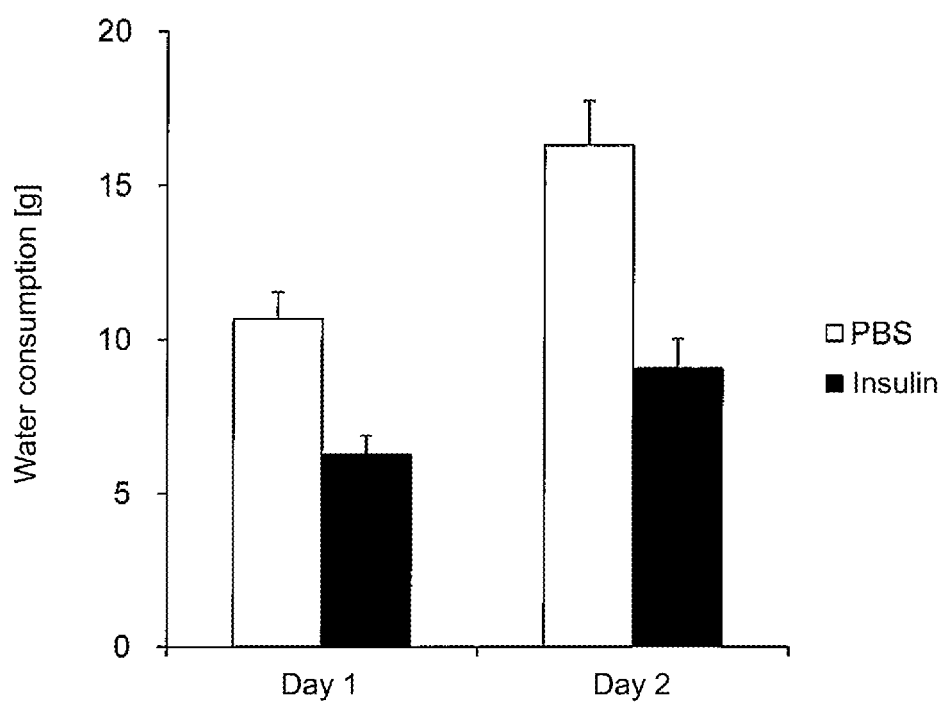
FIG. 10B is a chart showing the effect of suppressing water consumption in STZ-induced type 1 diabetes model mice, into which the drug delivery device in FIG. 2A filled with insulin or PBS was subcutaneously implanted.

As a result of observation of the water consumption of mice during the above test for 2 days, as indicated in FIG. 10B, the water consumption in the insulin delivery device group decreased significantly as compared to the control group, suggesting that symptoms resulting from hyperglycemia were suppressed.

INDUSTRIAL APPLICABILITY

The device of the present invention is electronics-free, and therefore, it can continuously control release of insulin by responding to variations in the blood sugar level of an individual patient without using a complicated algorithm while it is attached to the patient. Therefore, the device of the present invention does not require equipment necessary for a micro-computer controlled insulin pump, and thus, it is suitable for use in elderly patients and those in need of care or even for use in areas that are not well-equipped in developing countries, etc. In addition, the device makes it possible to control the amount of insulin to be released in accordance with the patient's physical conditions rather than administering daily in an automatic manner.

All publications, patents and patent applications cited in the present description are incorporated herein by reference in their entirety.

REFERENCE SIGNS LIST

1 Device
2 Catheter
3 Reservoir
4 Side wall
5 Side hole
6 Gel-filled portion
7 Drug-filled portion
8 Needle
9 Reservoir
10 Skin
11, 21, 31 Catheter
12, 22 Side hole
32 Opening

The invention claimed is:
1. A drug delivery device comprising a porous body having biocompatibility and drug permeability, a stimuli-responsive gel composition filling inside of the porous body, and a drug surrounded by the gel composition inside of the porous body, wherein the gel composition is a copolymer gel composition comprising N-isopropylmethacrylamide (NIPMAAm) and 4-(2 acrylamido-ethylcarbamoyl)-3-fluorophenylboronic acid (AmECFPBA),
wherein the porous body is in the form of a hollow fiber, wherein the hollow fiber is made of an ultrafiltration membrane, and the ultrafiltration membrane has a molecular weight cut-off of not more than 10,000 daltons, and wherein the porous body has an outer diameter of 100 to 2,000 µm, an inner diameter of 50 to 1,950 µm, and a length of 0.1 to 100 mm.

2. The drug delivery device according to claim 1, comprising a biocompatible drug release member having a drug release portion, a stimuli-responsive gel composition filling inside of the drug release member, and a drug surrounded by the gel composition inside of the drug release member, wherein the drug release portion releases the drug by diffusion based on the difference in drug concentration between the outside and the inside of the gel composition, wherein the gel composition is a copolymer gel composition comprising N-isopropylmethacrylamide (NIPMAAm) and 4-(2 acrylamido-ethylcarbamoyl)-3-fluorophenylboronic acid (AmECFPBA).

3. The drug delivery device according to claim 1, wherein the gel composition is a glucose concentration-responsive gel composition.

4. The drug delivery device according to claim 3, wherein the glucose concentration-responsive gel composition is a copolymer gel composition comprising a phenylboronic acid monomer as a monomer.

5. The drug delivery device according to claim 4, wherein the copolymer gel composition is formed using N,N'-methylenebisacrylamide (MBAAm) as a cross-linking agent.

6. The drug delivery device according to claim 1, wherein the drug is insulin.

7. The drug delivery device according to claim 1, wherein the drug is mixed in the gel composition.

8. The drug delivery device according to claim 1, wherein the porous body is inserted into a patient.

9. The drug delivery device according to claim 2, wherein the gel composition is a glucose concentration-responsive gel composition.

10. The drug delivery device according to claim 9, wherein the glucose concentration-responsive gel composition is a copolymer gel composition comprising a phenylboronic acid monomer as a monomer.

11. The drug delivery device according to claim 10, wherein the copolymer gel composition is formed using N,N'-methylenebisacrylamide (MBAAm) as a cross-linking agent.

12. The drug delivery device according to claim 2, wherein the drug is insulin.

13. The drug delivery device according to claim 2, wherein the drug is mixed in the gel composition.

14. The drug delivery device according to claim 2, wherein the porous body is inserted into a patient.

15. The drug delivery device according to claim 1, wherein the drug delivery device comprises 2 to 100,000 hollow fibers.

* * * * *